United States Patent [19]

Landon et al.

[11] 4,083,766

[45] Apr. 11, 1978

[54] APPARATUS TO DETECT TOXIC IONS IN THE ATMOSPHERE OR DISSOLVED IN WATER

[75] Inventors: Fred Landon, Cachan; Maurice Bonnemay, Boulogne; Jean-Pierre Laverge; Pierre Malaterre, both of Paris; Jean Royon, La Varenne, all of France

[73] Assignee: Etat Francais represente par le Deleque Ministeriel pour l'Armement, France

[21] Appl. No.: 485,731

[22] Filed: Jul. 3, 1974

[30] Foreign Application Priority Data

Aug. 7, 1973 France .................................. 73 28761

[51] Int. Cl.$^2$ ........................................ G01N 27/26
[52] U.S. Cl. ................................ 204/195 R; 204/1 T; 324/30 R
[58] Field of Search ................. 204/195 R, 1 T, 1 N, 204/271; 324/30 R

[56] References Cited

U.S. PATENT DOCUMENTS

| | | | |
|---|---|---|---|
| 2,864,747 | 12/1958 | Roth | 204/1 T |
| 3,451,901 | 6/1969 | Seiger et al. | 204/1 T |
| 3,470,071 | 9/1969 | Vertes et al. | 204/1 T |
| 3,471,393 | 10/1969 | Ingruber | 204/195 R |
| 3,586,608 | 6/1971 | Juda et al. | 204/1 T |
| 3,825,483 | 7/1974 | Nakamura | 204/1 T |
| 3,838,032 | 9/1974 | Yarnilsky | 204/1 T |
| 3,957,611 | 5/1976 | Moll et al. | 204/195 R |

*Primary Examiner*—Edward A. Miller
*Attorney, Agent, or Firm*—Stevens, Davis, Miller & Mosher

[57] ABSTRACT

A process to detect toxic ions in the atmosphere or dissolved in water with an electrochemical cell which comprises an active electrode, a reference electrode and a counter electrode, connected by an electrolyte and to which a voltage is applied.

The voltage alternates on each side of the thermodynamic potential. The cell, which is adapted to detect toxic gases in air, comprises a condensation chamber connected to a venturi for the admission of air and electrolyte, and to a measurement chamber. The electrolyte carrying the dissolved toxic gas is condensed in this chamber prior to passing through the measurement chamber.

The invention is applicable in particular to check the atmosphere of workshops, and to check the pollution of bodies of water with an independent portable unit.

2 Claims, 8 Drawing Figures

APPARATUS TO DETECT TOXIC IONS IN THE ATMOSPHERE OR DISSOLVED IN WATER

This invention concerns a process to detect ions, particularly toxic ones, diluted in the atmosphere or dissolved in water, by analysis of the support medium to reveal the presence of such ions, especially of anions such as cyanide or fluoride.

The invention concerns also a device to implement this process, such device to include in particular an electrochemical detection cell.

The detection of typical anions in a fluid is a problem to which a number of solutions have been applied and of which solutions, the voltametric methods are an important category. The principle of such methods consists of measuring the current produced by a given difference of potential applied to the electrodes of a voltameter.

The detection of the presence of an anion is based on the fact that under certain conditions the metal of the active electrode can form a complex with such anion, which phenomenon results in a significant change in the electrolysis current. More precisely, a known method, called the stationary method, consists of passing through an electrochemical cell, a steady reflux of a mixture of the fluid to be observed and of the electrolyte, while the voltage at the cell terminals is kept constant and equal to the specific potential of the anion with the electrode metal. Under such conditions, the electrolysis current which would remain constant with pure electrolyte, shows more or less accentuated peaks each time the anion occurs in the mixture. The detection is drawn out of such changes by recordings.

The presence of hydrocyanide gas in air is detected by passing air through a platinum and silver electrode cell. The cyanide ions form a complex with the silver and such complexing generates between the electrodes, a difference of potential evidenced as a multivoltmeter. The main drawback of such method is that it alters the active electrode. Such alteration can be either a passivation in which case the anion to be detected may be present but pass undetected, or an oxidation in which case spurious signals may be produced and trigger alarms even though the anion is not present.

Another drawback of such method is its lack of selectivity regarding anions with slightly differentiated complexing potentials.

This invention intends to palliate such drawbacks by preventing, on the one hand, the irreversible alteration of the active electrode and on another hand, by permitting detection of the anions with a good selectivity, which complexing or typical potential is quite close to one another.

According to this invention process, to detect toxic ions either in the atmosphere or dissolved in water, with an electrochemical cell which comprises an active electrode and a reference electrode to which a voltage is applied, a toxic gas ion forms a complex with the active electrode metal.

According to this invention, such process is characterized in that an alternating voltage is applied to the active electrode, which voltage varies both over and under the complexing potential of the active electrode metal with the ion to be detected, and on either side of the thermodynamic balance potential. The presence of such ion in the electrolyte is detected by observing and recording the electrolysis current changes induced by the above mentioned complexing. Above the thermodynamic balance potential, the active electrode functions as an anode while under such potential it functions as a cathode, which permits the regeneration of its surface during the cathodic phase. A significant and durable alteration of the active electrode is thus prevented. A third electrode, called a counter-electrode, operates as an election trap and will allow evaluation of the current necessarily provided by a potentiostat to maintain the various potentials applied to the active electrode during the potentiostatic sweep.

According to a particular implementation of the process, the intensity peak is memorized. Such peak can also be integrated according to time or according to the applied voltage, and such integration also may be memorized.

According to an advantageous feature of the process intended to detect anions with small differences in their complexing potentials, the applied voltage is modulated in time, in such a way that in the area of complexing potentials, the potential variation grade is approximately proportional to the difference between such potentials. The process selectively is thus improved.

According to a particular application of the process, a substance susceptible, on the one hand to complex with the electrode, and on the other hand, to react with the toxic to be detected is added to the electrolyte. The intensity peak which would be observed without any toxic, is suppressed or reduced if the toxic ion is present.

The device to implement the process consistent with the invention, in particular, to detect and measure the toxic gas concentration in the atmosphere comprises an electrochemical cell with an active electrode and a reference electrode protruding in a measurement chamber, means to introduce and remove an electrolyte in such cell and an electronic system to measure the toxic gas concentration in the atmosphere, connected to the electrochemical cell, and a measurement display device.

According to this invention, such device is characterized in that the electrochemical cell comprises an electrolyte condensation chamber communicating with the measurement chamber on the one hand and with a suction circuit on the other hand.

Such disposition permits stabilization of the electrolyte before it is introduced in the measurement chamber and ensures the complexing process of the toxic ion under good conditions.

According to a preferred implementation of the invention, the cell comprises a gas and electrolyte venturi inlet tube connected to the condensation chamber, such tube being equipped with an adjustable needle valve. The electrolyte/toxic gas mixture is hence admitted as a mist in the condensation chamber and settles on the chamber walls.

According to a preferred implementation of the invention, the internal walls of the condensation chamber are polished with the condensation chamber being connected to the measurement chamber through a duct having a small dimension as compared to that of the condensation chamber.

The duct completes the condensation chamber and suppresses any detrimental turbulence of the toxic ion carrying the electrolyte prior to its admission in the measurement chamber.

Figure 1:
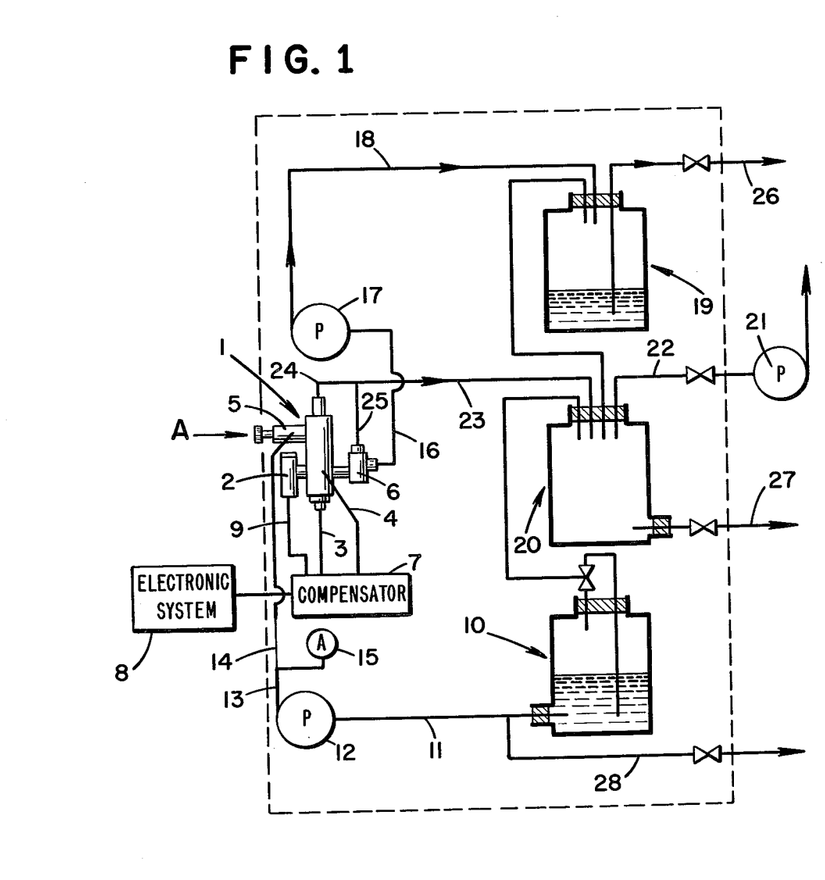
FIG. 1 is a schematic of the device of the present invention intended for the detection of toxic gas in the atmosphere.
Figure 2:
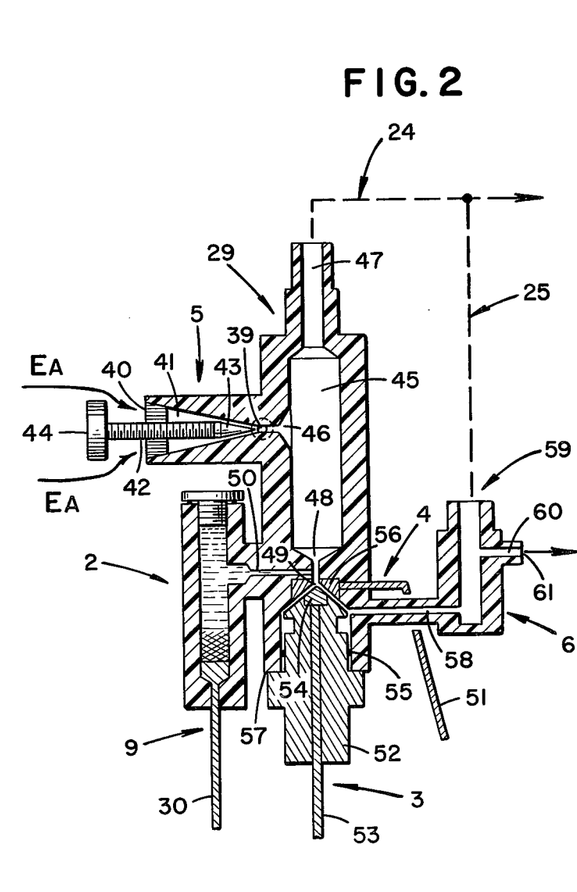
FIG. 2 is a cut-away view of the electrochemical cell pertaining to FIG. 1.

In the implementation of FIGS. 1 and 2, an electrochemical cell 1 is fitted with a reference electrode 9 which ends in a chamber 2, with an active electrode 3 and with a counter-electrode 4. Such electrodes are further connected to an impedance compensator 7 which is in turn connected to an electronic measurement system 8 hereinafter described.

A drainage tank 6 is connected through a pipe 16 to the suction end of a drainage pump 17. This pump is a dosimetric pump, of the roller type for instance, and it is regulated to operate at a constant speed. Its outlet is connected through a pipe 18, to a drainage tank 19 which can be periodically drained through a pipe 26.

The cell 1 is further provided with a venturi inlet for the simultaneous admission of air and electrolyte. It is connected through pipes 24 and 25 to a suction collector 23 which opens in a retention tank 20 from which any eventual liquid drawn can be drained through pipe 27. A pipe 22 is connected to the suction inlet of pump 21.

The electrolyte inlet opening in the venturi 5 is connected to the outlet of a pump 12 through a pipe 13 which includes a capilary 14. An air tank 15 is connected to pipe 13. Pump 12 is of the same type as pump 17 or of a similar type. Pump 12 is connected through a suction pipe 11 to an electrolyte storage tank 10 which can be periodically filled through pipe 28.

FIG. 2 shows a detailed view of cell 1. Such cell is essentially comprised of a plastic body 29 which includes the chamber 2 for the reference electrode 9, the air and electrolyte inlet venturi pipe 5 and the electrolyte draining tank 6.

These three above mentioned parts (2, 5, 6) can be manufactured either in one body or in three separate parts to be assembled.

A cable 30 connects the reference electrode 9 to the impedance compensator 7 and to the potentiostat 8; the reference electrode 9 with standard potential, is of the well known Hg/Hgo type and is connected to a measurement chamber 49 through an electrolytic bridge 50.

The venturi 5 has a conical nozzle 41 closed with a filtering disk 40 which is threaded in its center to support the threaded shank 42 of an adjustable needle 43 which can be operated with a knurled knob 44. The electrolyte inlet 39 opens at the venturi throat which has for instance a diameter of one millimeter.

The throat of venturi 5 opens into a cylindrical condensation chamber 45 through a divergent section 46. The walls of this chamber 45 are carefully polished and its length could advantageously be 40 mm and its diameter 11 mm. It is connected on the one hand to suction pipe 24 through an opening 47 and on the other hand to the measurement chamber 49 through a duct 48. The diameter of duct 48 could typically be 0.7 mm.

The electrolyte bridge 50 connects the cavity of chamber 2 having the reference electrode 9 with the measurement chamber 49 through part of duct 48. The electrochemical cell has further a counter-electrode 4, preferably made of platinized titanium having an active part 56 which is ring shaped. It is centered on the axis of the condensation chamber 45 and press fitted into the body 29 so as to be located at the end of duct 48. It presents a hollow cone on its face opposite to the duct 48 and is connected by usual means to lead 51.

A mobile cylindro-conical sleeve 52 has a lead 53 passing through it along its axis, the end of which lead is connected to the active part 54 of the active electrode 3. Such active part 54 is made of gold and has a conical shape. A shoulder 57 on sleeve 52 rests against the body and provides a space of about 0.5 mm between the salient cone of part 54 of the active electrode and the hollow cone of part 56 of counter-electrode 4. Such space constitutes the measurement chamber 49. Tightness is provided by a ring 55.

The drainage tank 6 is connected to the measurement chamber 49 through a duct 58. It is also connected to the suction pipe 25 by its end 59 and to suction pipe 16 through a cylindrical duct 60. The lower generatrix 61 of this duct is at approximately the same level as the connecting point of duct 48 with the condensation chamber 45.

The operation of such device is as follows:

Due to the vacuum created by pump 21 (FIG. 1) and transmitted through pipes 22, 23 and 24, the atmospheric air to be tested is drawn into the venturi 5 in the direction shown by arrows EA. The flow of air admitted is adjusted with the needle 43.

Further, the dosimetric pump 12 draws a constant flow of pure electrolyte from tank 10 through pipe 11. On discharge pipe 13, a capilary 14, in cooperation with the air tank 15 regulates the pulsating character of the flow resulting from the type of pump used. This electrolyte is then brought to the venturi 5 throat through inlet 39 (FIG. 2). The venturi effect atomizes the electrolyte to fine droplets which dissolve part of the toxic gas and further coalesces in part on the walls of condensation chamber 45. The polluted electrolyte runs down by gravity along the polished walls and collects in duct 48. The mist laden air, cleared of toxic is drawn through outlet 47 towards pipes 24 and 23, the retention tank 20 being intended to hold any drawn liquid.

Still by gravity, the polluted electrolyte passes through the measurement chamber 49 and is drained out through duct 58 to drainage tank 6 where duct 60 functions as an overflow to keep the liquid level at approximately the same level as the opening of duct 48. Such overflow effect is achieved through equilization of air pressures in chamber 45 and in tank 6 by connection of pipe 24 to the tank inlet 59 through pipe 25.

The polluted electrolyte which passes through duct 60 is sucked by the dosimetric pump 17 having a speed which is adjusted to give a slightly higher flow than that of pump 12. Pump 17 further discharges the polluted electrolyte towards the drainage tank 19.

It can be seen from the above described performance that the benefits drawn from such a disposition are a constant flow of electrolyte associated with a constant flow of the air to be analyzed. Moreover, one of the advantages of cell 1 according to the invention is to provide a good contact between air and liquid through atomization and to provide further an efficient separation of the gaseous and liquid phases as well as a minimal turbulence of the liquid in the electrolyte chamber.

Figure 5:
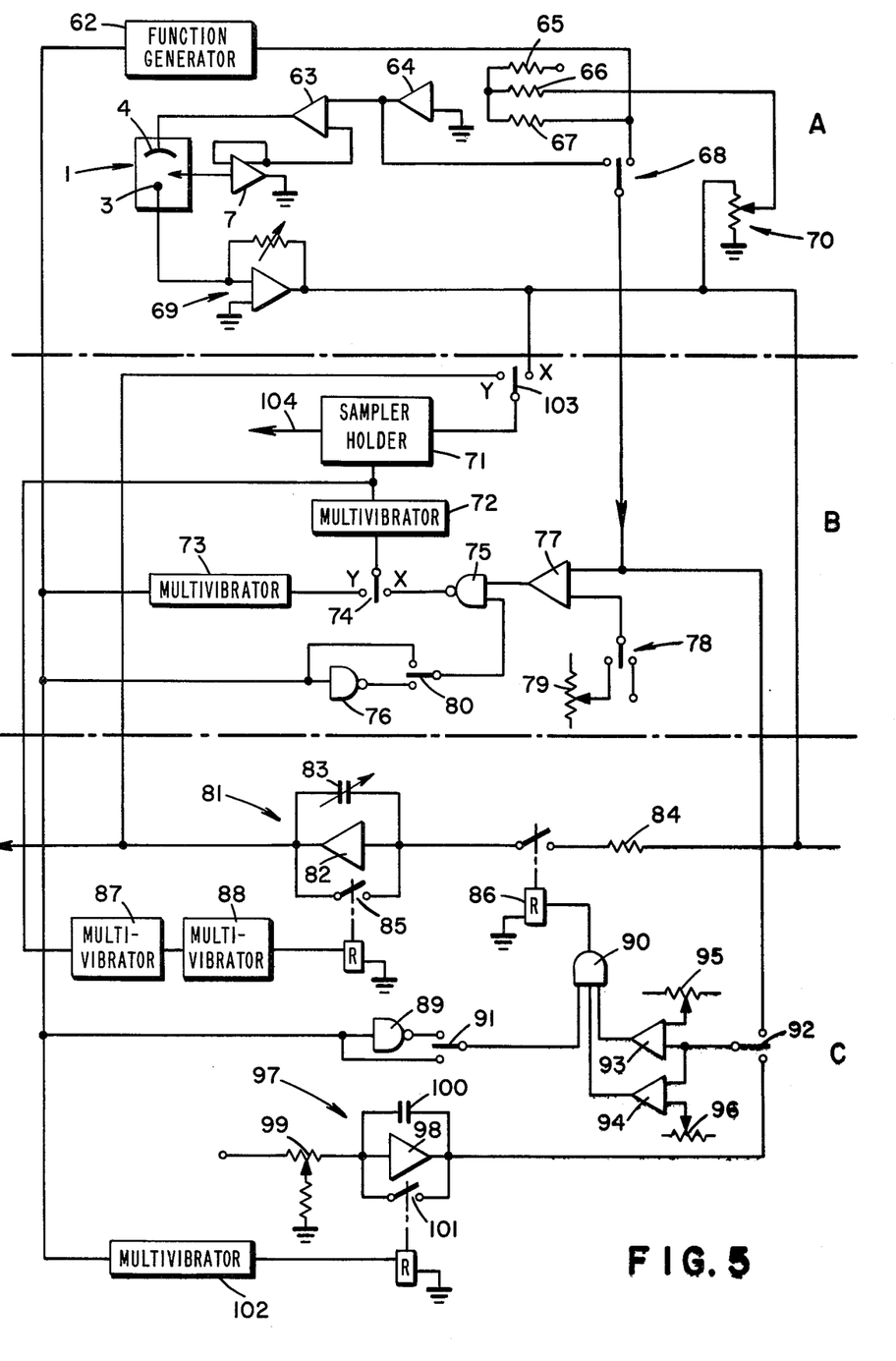
FIG. 5 is a detailed schematic of the electronic system of the devices shown on FIGS. 1 to 4.

The impedance compensator 7 can be made a part of the electrochemical cell 1. However, for a better understanding, FIG. 5 shows all the electrical devices, that is the impedance compensator 7 and the electronic system 8, as well as a schematic of cell 1.

The electronic system 8 will now be described with reference to FIG. 5.

The upper part A shows the potentiostatic device 5 itself which comprises a function generator 62, the impedance compensator 7 connected to the reference electrode 9, a comparator 63, an amplifier-mixer 64, fixed value resistances 65, 66 and 67, a manual switch 68, a variable negative reaction amplifier 69 and a potentiometer 70.

Part B of the electronic system shows the sampler-holder 71 and its associated components which includes monostable multivibrators 72 (fixed) and 73 (adjustable), hand operated switches 74, 78 and 80, a "NAND" gate 75, an inverter 76, a comparator 77 and a potentiometer 79.

Part C of the system shows an integrator 81 and its associated components.

Integrator 81 comprises an amplifier 82 cooperating with an adjustable capacitor 83 and a fixed value resistance 84. Part C also comprises relay switches 85 and 86. The associated components comprise monostable multivibrators 87 and 88, inverter 89, an "AND" gate 90, hand operated switches 91 and 92, comparators 93 and 94 and potentiometers 95 and 96.

A ramp generator 97 comprises an amplifier 98 cooperating with potentiometer 99 and capacitor 100, a relay switch 101 and a bistable multivibrator 102.

The operation of the above described electronic system 8 is as follows:

The potential of the reference electrode 9 is adjusted under low impedance with compensator 7, then compared to the design potential in the comparator 63. A booster composed of a symetrical solidstate stage (not shown) supplies the required voltage to maintain at a null value the error signal detected by comparator 63.

The design potential is provided at the output of the amplifier-mixer 64. The latter is an integrator of the voltages defined by ohmic resistances 65, 66 and 67 energized through the potentiostat not shown. If only resistance 67 is energized, there is a non-mixed design potential. The signal picked on the active electrode 3 gives at the output of the reaction amplifier 69 a voltage which represents the electrolysis current intensity.

Potentiometer 70 which provides to the amplifier mixer 64 part of the measurement image voltage, serves to correct the variable ohmic drop in the measurement chamber 49.

When switch 103 is on position X, the signal which represents the electrolytic current intensity is applied to the input of the sampler-holder 71.

Figure 6:
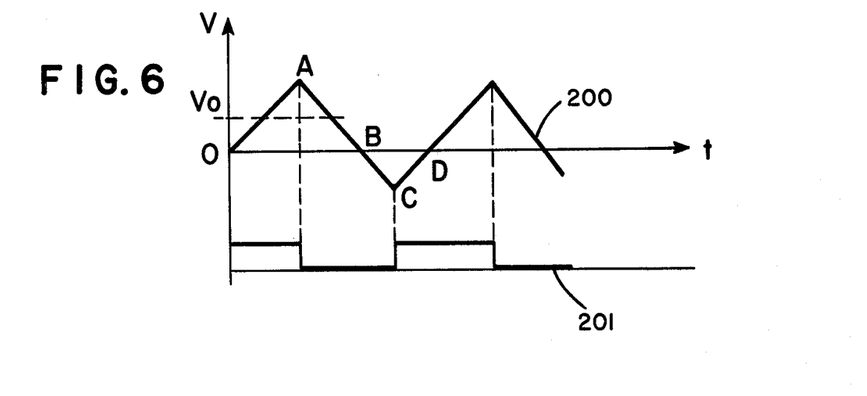
FIG. 6 is a diagram of electrode potential variations.

The operation of this equipment is controlled in the following manner. The design potential (mixed or not according to the position of switch 68) is compared in comparator 77 to a "sampling" potential which can be either fixed and preset with potentiometer 79 or programmed through a device not shown, according to switch 78 position. It is here assumed that switch 74 is on position X. The comparator 77 output logic level goes from 0 to 1 if the design potential equals the sampling potential and triggers multivibrator 72 provided the "NAND" gate 75 is validated by the synchronization signal provided by the function generator. Such signal has a value 1 when the generator supplied potential increases, and a value zero when this potential decreases. In FIG. 6, curves 200 and 201 represent respectively the variation of the design potential and the synchronization signal as a function of time. The combination of the inverter 76 and of switch 80 will allow sampling in the rising phase of the design potential (going up) or in the decreasing phase (going down). In the above described example, the control pulse provided by multivibrator 72 lasts approximately 0.1 ms.

If switch 74 is set on position Y, sampling is no longer determined by the design potential but by time; in such case, the synchronization signal activates adjustable delay monostable multivibrator 73 which in turn controls multivibrator 72.

The sampler-holder 71 output signal 104 can be either stored on a recording or shown on a visual display monitor.

The operation of integrator 81 will now be described:

Integrator 81 can be switched on with switch 86. Its operation is combined with that of the sampler-holder 71, switch 103 being set on position Y. The signal representing the electrolysis current intensity is applied to the input of integrator 81. The output signal of integrator 81 is applied to the input of sampler-holder 71 which takes charge of the integrated electrolysis current. The sampling is performed as described earlier. Further, multivibrator 72 which triggers the sampling also controls the resetting to zero of integrator 81 through relay switch 85 and multivibrators 87 and 88 in which a delay action permits a reading of the measurement before fading out.

The integration terminals can be controlled on the one hand depending on the electrode potential compared in comparators 93 and 94 to potentials preset on potentiometers 95 and 96, and on the other hand depending on time through adjustable slope ramp generator 97 controlled with potentiometer 99. The triggering of the ramp generator 97 is done with switch 101 controlled with bistable multivibrator 102 which receives the synchronization signal. The selection between these two possibilities is made with switch 92.

As in the control of sampler-holder 71, the control of integrator 81 must be validated in gate 90 by the synchronization signal, inverted or not in the inverter 89 according to the setting of switch 91.

The following detailed description will permit an easier understanding of the process of the present invention.

A bath solution is made with pure electrolyte polluted with a certain quantity of the fluid to be analyzed. In most cases an analysis is made, in a continuous mode with constant flows and a fixed ratio of the two above mentioned components, i.e., electrolyte and fluid, the measurement chamber 49 being the seat of a regular flow of fluid.

Such conditions being assumed, the electrolysis is performed by the application, between the reference electrode 9 and active electrode 3, of a difference of potential varying periodically in time through the potentiostatic device previously described with reference to FIG. 5. In FIG. 6, curve 200 represents such a variation called triangular scanning.

Figure 7:
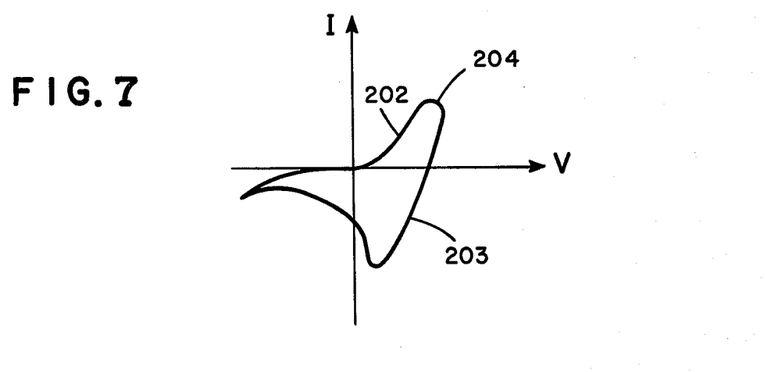
FIGS. 7 and 8 are diagrams of electrolytic current intensity for two particular examples.

When the increasing potential of the active electrode 3 reaches a value Vo characteristic of the ion to be detected, there occurs a complexing between the ion and the metal of electrode 3 acting as an anode which produces a peak on the curve showing the intensity of the electrolysis current as a function of time. It is often preferred to consider the intensity curve as a function of the potential, which is a quite common notion, since the potential is a perfectly known and often very simple, for instance linear, function of time. Such a curve is shown in FIG. 7, for a particular example. Arc 202 corresponds to the increasing potential (going up) and arc 203 to the decreasing potential (going down). There is generally some dissymmetry between the two arcs.

In FIG. 6, reference zero of the electrode 3 potential corresponds to the thermodynamic neutrality potential. One of the characteristics of the process of the present invention is to have the potential decrease to a lower value than the neutrality potential in order that during the time interval corresponding to portion BCD of the curve, the polarity of the active electrode 3 be inverted, such inversion resulting in a cathodic regeneration of the surface of the active electrode 3 altered by complexing at Vo potential. The relative duration of the active and of the regeneration phases can be adjusted with the above mentioned potentiostatic devices.

Figure 8:
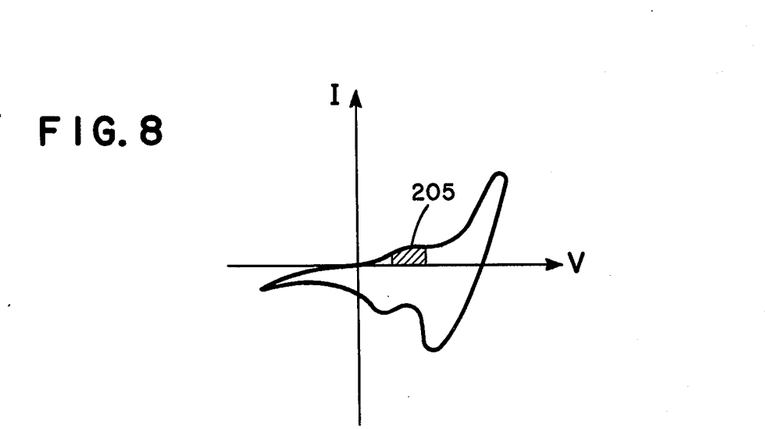

The simplest way to effect a measurement consists of sensing and memorizing the height of the intensity peak with the sampler-holder device previously described. Should a more accurate measurement be required, in particular if the peak is not very conspicuous such as peak 205 of FIG. 8, it will be preferable to integrate such peak (shaded area), than to sense and memorize the result of such integration.

The potential variation period is approximately one second. Should it be desired to detect several anions with not much differentiated complexing potentials, it will be advantageous to adopt a slow variation of potential and to program a time related sampling. To prevent an excessive lengthening of the period, the slow variation can be limited to only part of the period through application of a relatively complex variation rule, implemented with the potentiostatic devices previously described.

It may in some cases be advantageous to adopt a deviation of the process, called the "return method", which consists of adding to the electrolyte a substance that will by its mere presence produce a peak in the curve and which at the same time will react with the pollutant. The eventual presence of pollutant is then evidenced by the disappearance or attenuation of the above mentioned peak. The substance to use for the detection of the cyanide ion could for instance be iodine.

Further, the measurement is improved if the active electrode 3 is made of a metal which has particular reactive affinities with the toxic to be detected.

Figure 3:
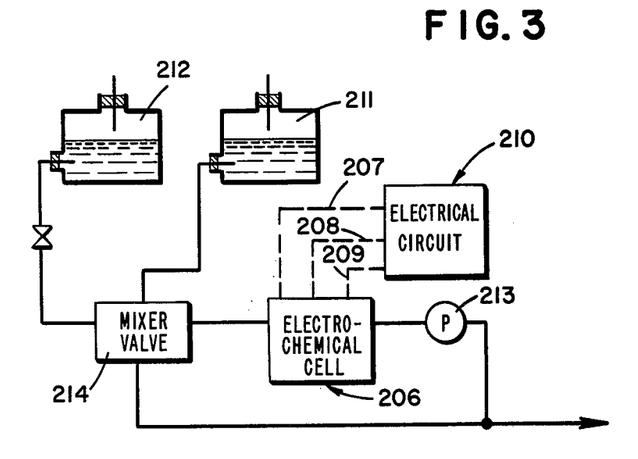
FIG. 3 is a schematic of the device of the present invention intended for the detection of toxic gas dissolved in water.

FIG. 3 represents a modified version of the device shown on FIG. 1 and previously described, but which is here applied to the research of toxics dissolved in a liquid such as water. It comprises an electrochemical cell 206 with three electrodes 207, 208 and 209 connected to an electrical circuit 40, supply tanks 211 and 212 which contain respectively pure electrolyte and the liquid to be tested, a dosimetric circulation pump 213 and a mixer valve 214 of the type used in chromatography.

All these components are identical to the corresponding parts shown on FIG. 1, except for the valve 214 and the cell 206.

Figure 4:
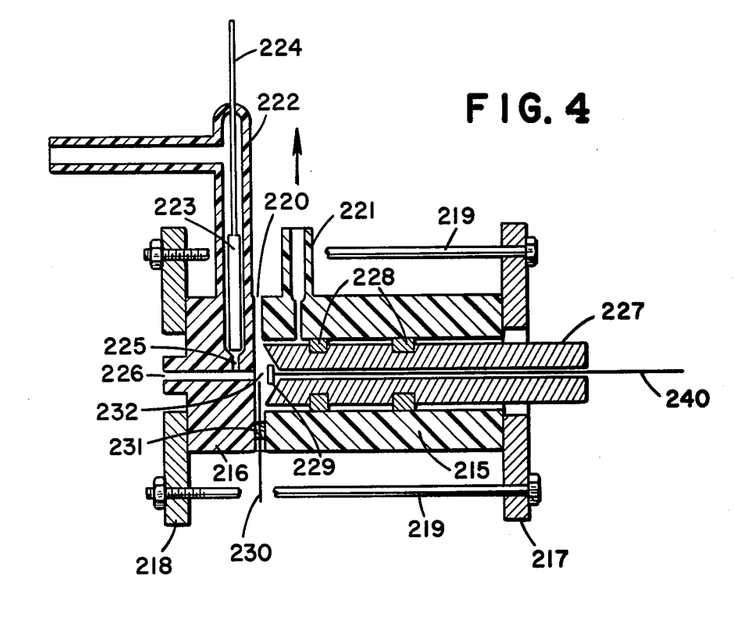
FIG. 4 is a cut-away view of the electrochemical cell pertaining to FIG. 3.

The cell 206, shown on FIG. 4 consists of a plastic body in two parts 215 and 216, separated by a ring seal 220 and held tightly together with two plates 217 and 218 fastened together with the bolts 219. Part 215 has bored along its axis a protruding outlet 221 bored down to the boring.

Part 216 has a protruding lateral tube 222 having a branch which is attached to part 216 that holds the active part 223 of the reference electrode. This active part is connected to a lead 224 which exits from tube 222 through an outlet which is made tight by known means. The same branch of tube 222 is connected through a duct 225 to an axial duct 226 in part 216. The other branch of tube 222 is an outlet.

A sleeve 227 fitted with ring seals 228 is engaged, with some play, into the axial boring of part 215. Through its axis passes a lead 240 connected to the active part 229 of the active electrode. The inside end of the sleeve is a hollow cone 232 which forms the measurement chamber.

A lead 230 passes through the ring seal 220 and is connected to the ring shaped counter electrode 231.

The operation of this device is as follows:

Pump 43 draws a constant flow of polluted electrolyte and discharges it on the outside. The suction occurs in the cell through outlet 221 and provides a flow of liquid in the measurement chamber 232 through the space provided between the sleeve 227 and the boring of part 215.

The inflow of liquid is provided through duct 226 from valve 214. The latter, supplied from tanks 211 and 212 assumes the same function as in chromatography, e.g., provides a precise quantity of the liquid to be tested versus pure electrolyte.

The operation of the measurement device is identical to that previously described regarding the equipment intended for the detection of toxic gas in air.

There will now be described, for information purposes, a few numerical examples of the implementation of the process and of the device according to the invention. Example No. 1:

Detection of cyanide ion in air with a gold electrode (implementation of FIGS. 1 and 2). Two aurocyanide complexes can be produced depending on the potential applied to the active electrode 3.

$Au(CN)_2$; $Au(CN)_4$

The active electrode 3 is made of polycrystalline gold wire of 2 mm diameter previously processed by anodic pickling in a bath of KCN at 70 grams per liter, of potassium and sodium tartar at 16 grams per liter. A potential of 12 volts is applied for one minute to this bath in which is immersed the gold electrode, and then the electrode is rinsed in distillated water.

The counter electrode 4 is made of platinum wire of 1 mm diameter and 8 cm length.

The electrolyte introduced in the condensation chamber 45 of cell 1 is a solution of potassium with a concentration of $10^{-2}M$.

The potential of the gold electrode 3 in which active part 54 has an area of 60 mm$^2$ is measured against that of a reference electrode similar to the one previously described (Hg/HgO/KOH) in a bath of KOH at $10^{-2}M$. All the above indicated potentials consequently are measured against the standard electrode Hg/HgO.

The voltage on the triangular scanning potential terminals may vary within certain limits depending on the operating conditions. Such potential may vary between +300 and −1200 mV, +500−1200 mV etc., with a scanning rate of 200 mV/s.

The flow of electrolyte within the measurement chamber 49 is of 1 cm³/mn, the volume of the chamber being approximately 0.1 cm³.

Under such conditions, peaks of electrolysis current due to the presence of cyanide in the electrolyte are detected within the range of −200 mV to +500 mV.

Hence at +300 mV for a concentration threshold of cyanide in air of 27 mg/m³.

Conjointly with the production an aurocyanide complex is produced an oxidized compound which gives an oxidation peak closely similar to the complexion peak to be detected. Such oxidation peak may hamper the detection and recording of the cyanide complexing peak and it may be advantageous to use the inhibiting properties of substances such as iodide or bromide KI, BrI ions, in such cases.

It is effectively noted that peaks corresponding to the presence of cyanide within the range −200 to +300 mV are more clearly separated in the presence of bromide or iodide previously added to the electrolyte. It is further noted that such separation is more accentuated with iodide when the scanning rate is increased.

Experience has also demonstrated that the base used as an electrolyte to carry the toxic ion has no influence on the measurement sensitivity. Either KOH or NOH may be used but the concentration must not exceed 0.1M; otherwise the sensitivity decreases.

It is further useful to add a neutral electrolyte which is only feebly adsorbed on the active electrode such as $K_2SO_4$ at approximately 100 grams per liter. Such addition increases the solution conductivity and thus decreases the antenna effect with respect to Hertzian spurious noises.

In the non limitative example of cyanide detection the current peaks may be either directly sampled or sampled after integration as previously explained. The following optimal conditions have been determined by testing:

(a) Direct sampling of the peaks:
  Electrolyte:
    KOH $10^{-1}$M,
    $K_2SO_4$ saturated, 100 g/l
    KI $10^{-2}$M
  Control signal: Triangular voltage
  Voltage scanning terminals:
    +350 mV ± 20 mV
    −1050 mV ± 50 mV
  Anodic scanning rate: 7V/s
  Cathodic scanning rate: less than 1.4 v/s
  The current peak is sampled at 230 ± 20 mV (in the anodic scanning mode).

(b) Sampling after integration of the peaks:
  Data (a) are also valid with the following integration terminals: +50 ± 20 mV to +350 ± 20 mV (in the anodic scanning mode)

Example No. 2:

Detection of cyanide ion with a silver electrode

With cyanide ions and a base, silver produces the following complexes:

$Ag(CN)_2$, $Ag(OH)(CN)$

The active electrode is a polycrystalline silver wire of 2 mm diameter with an active area of 60 mm², prepared by anodic pickling in a KCN bath at 70 g/l with a voltage of 1.5 to 2 volts, and carefully rinsed.

It is noted that under certain scanning conditions a drift of the thermodynamic neutrality potential occurs. Tests have shown that such drift could practically be eliminated with the addition of borate ions, while an excess of borate versus the base concentration would inhibit complexion of the silver by the cyanide.

The following parameters may be retained:
  Electrolyte: KOH M.
  Triangular scanning voltage.
  Anodic scanning rate: 2 ± 0.5 V/a.
  Cathodic scanning rate: 0.5 to 1 V/a.
  Peak sampled at −60 mV.

The detection threshold of cyanhydric gas in air is similar to that with the gold electrode.

REMARKS

Substances such as sulphur dioxide, hydrogen sulphide and carbon monoxide are oxidable at the gold or silver electrode and also generate peaks.

It has been observed that the response of the electrochemical cell according to the present invention, with a gold electrode, to the anion $SO_3$ under a concentration of $10^{-2}$M was equivalent to a cyanide concentration of $10^{-5}$M.

Such result corresponds to a selectivity of approximately 1000 times higher for cyanide than for sulphur dioxide.

The silver electrode selectivity is approximately 100 times higher.

The response time of the detection and measurement device according to the present invention is approximately 5 seconds and is determined based on the time the electrolyte passes from the venturi 5 to the active electrode 3.

The application of the present invention is not limited to the above described examples and may be varied. For instance, cyanide in the atmosphere can be detected with a platinum active electrode 3, and other toxic substances such as certain organo-phosphorate compounds which are ionizable in water can also be detected.

Thus the invention applies to any toxic ions voluntarily or accidentally diffused in the air or in water and susceptible to produce a reaction of any nature (electrochemical, adsorbtion, etc.) which results in a specific change of one voltamogram for a given electrode.

The device provided by the invention may be installed on an electric battery and so constitutes an easily portable unit to detect toxic ions promptly "in situ".

Such unit is particularly interesting for measuring atmospheric pollution, streams and bodies of water with toxic products such as those indicated.

What is claimed is:

1. Apparatus for detecting and measuring the atmospheric concentration of toxic gases, comprising:
  an electrochemical cell having a measurement chamber, an active electrode and a reference electrode located in said measurement chamber, means for introducing an electrolyte into said measurement chamber and for draining said electrolyte after a measurement, an electrolyte condensation chamber communicating with said measurement chamber and with a suction circuit, and a venturi tube having an adjustable needle valve for admitting gas and electrolyte into said condensation chamber;
  means connected to said electrochemical cell for electronically measuring the concentration of toxic gas in the atmosphere; and means coupled to said measuring means for displaying the results of a measurement.

2. Apparatus for detecting and measuring the atmospheric concentration of toxic gases, comprising:
an electrochemical cell having a measurement chamber, an active electrode and a reference electrode located in said measurement chamber, means for introducing an electrolyte containing a toxic ion into said measurement chamber in communication with said active and reference electrodes, means for draining said electrolyte after a measurement, an electrolyte condensation chamber communicating with the measurement chamber and with a suction circuit, and a venturi tube including an adjustable needle valve to admit gas and electrolyte into said condensation chamber;
measuring means connected to said electrochemical cell for electronically measuring the concentration of toxic gas in the atmosphere, said measuring means including means for applying a potential to the active electrode to provide a potential difference between said active and reference electrodes, said potential alternating on each side of the complexing potential of the active electrode with the ion to be detected and of the thermodynamic neutrality potential, and means for detecting the presence of said ion in the electrolyte by measuring and recording the electrolysis current change produced by the complexing of said toxic ion with said active electrode, said active electrode being a metal; and
means coupled to said measuring means for visually displaying the results of a measurement of said current change.

* * * * *